United States Patent [19]

Haber et al.

[11] Patent Number: 5,395,326

[45] Date of Patent: Mar. 7, 1995

[54] PHARMACEUTICAL STORAGE AND MIXING SYRINGE HAVING HIGH PRESSURE ASSISTED DISCHARGE

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 140,288

[22] Filed: Oct. 20, 1993

[51] Int. Cl.⁶ .................... A61M 37/00; A61M 5/00; A61M 5/315

[52] U.S. Cl. .................... 604/90; 604/191; 604/219; 604/237

[58] Field of Search .................... 604/82, 85, 89, 90, 604/187, 191, 219, 221, 222, 228, 230, 236, 237, 207, 416, 56

[56] References Cited

U.S. PATENT DOCUMENTS

| | | | |
|---|---|---|---|
| 728,160 | 5/1903 | Chappell | 604/219 |
| 729,011 | 5/1903 | Tagliabue et al. | 604/219 |
| 814,543 | 3/1906 | Horner | 604/219 |
| 3,058,467 | 10/1962 | Faure | 604/90 X |
| 3,164,303 | 1/1965 | Trautmann | 604/89 X |
| 3,342,180 | 9/1967 | Sandhage et al. | 604/89 |
| 3,511,239 | 5/1970 | Tuschhoff | 604/89 |
| 4,109,653 | 8/1978 | Kozam et al. | 604/191 |
| 4,673,395 | 6/1987 | Phillips | 604/191 |
| 4,689,042 | 8/1987 | Sarnoff et al. | 604/89 |
| 5,067,948 | 11/1991 | Haber et al. . | |
| 5,114,411 | 5/1992 | Haber et al. . | |
| 5,147,323 | 9/1992 | Haber et al. | 604/191 |
| 5,211,285 | 5/1993 | Haber et al. . | |
| 5,240,146 | 8/1993 | Smedley et al. . | |
| 5,281,198 | 1/1994 | Haber et al. . | |

*Primary Examiner*—John D. Yasko
*Assistant Examiner*—Adam J. Cermak
*Attorney, Agent, or Firm*—Townsend & Townsend Khourie & Crew

[57] ABSTRACT

A hand held syringe has a stationary handle and a moving handle to enable both stored and transported pharmaceuticals to be mixed and injecting the mixed pharmaceuticals under high pressure immediately after mixing through a long needle to a site interior of the body. The syringe is provided for squeeze grip at the stationary and moving handles between fingers and palm and includes a jell storage chamber side-by-side with a diluent storage chamber. Upon initial compression of the handles towards one another against a spring bias, the diluent discharges to the jell mix chamber along a one way path. At the same time, a handle actuated piston with loosely fitting O-ring in the jell mix chamber moves through the jell and introduced diluent effecting mixing movement by allowing the jell and diluent to flow between the piston and jell chamber sidewalls. Flow occurs from the jell chamber by the piston to an expansible chamber delimited by a floating seal. When injection is desired, the syringe is fully expanded against the spring bias and an O-ring on the reciprocating piston is tightened to radially dilate the O-ring to effect sealed wiping of the jell chamber. When full dilation of the O-ring has occurred, the long needle replaces a sealing plug at the distal end of the jell chamber of the syringe and injection occurs under the full squeeze force developed by the digits against the human palm.

29 Claims, 4 Drawing Sheets

PHARMACEUTICAL STORAGE AND MIXING SYRINGE HAVING HIGH PRESSURE ASSISTED DISCHARGE

This invention relates to a syringe for the storage and transport of pharmaceuticals which typically must be mixed immediately before injection. Specifically, a hand held syringe assembly is disclosed which enables mixing immediately prior to injection. Additionally, the syringe provides for the full grip of the hand to be used for distal injection to the human body with needles of length in the range of seven inches.

BACKGROUND OF THE INVENTION

Certain pharmaceuticals for injection must be stored and transported in a jell format. Unfortunately, these pharmaceuticals in the jell format are too viscous for direct injection. Some of these jells are utilized in chemotherapy.

A preferred jell here used would comprise a cytotoxant and a bulking agent. A preferred low viscosity diluent would comprise a vaso-constricting agent. The jell or high viscosity factor contains a cytotoxin mixed with a biocompatible bulking agent. The diluent or lower viscosity factor comprises a vaso-constrictor to inhibit blood supply to the tumor.

Presence of the bulking agent structures stabilizes the location of the implant within the tumor so as to retain the most effective positioning for the most protracted time period possible. Unfortunately, this effect is of short duration. Thus mixing is required immediately prior to injection. By way of example, a common injected dosage included 9 cc of jell with 0.9 cc of diluent.

The present solution to this problem is to package, store and ship the diluent in one syringe and the jell in another syringe. Immediately before injection, the two separate syringes are opened and connected to a mixing manifold. Thereafter, injection to and from each syringe occurs. Finally, when mixture has occurred, substantially all of the mixed jell and diluent is injected to one syringe—for example the syringe that originally transported the jell. Thereafter, injection conventionally occurs.

The manipulation of two separate glass syringes to a separate fitting immediately prior to injection is burdensome and unduly complex for the modern medical environment. What is needed is a unitary assembly which is self contained and user friendly to the required mixing.

With these pharmaceuticals, another problem exists. Specifically, they must sometimes be injected at relatively great depth into the human body. For example, in certain chemotherapy applications, relatively viscous solutions are utilized to inject and thereafter hold the chemotherapy solutions adjacent a tumor site. Unfortunately, such injection must occur through a long (in the range of seven inches) needle. This requires power for injection that cannot be conveniently supplied by a single digit—without the person administering the dose have discomfort accompanied by both fatigue and effort tremulation of the injecting digit and hand. The device of this disclosure is directed specifically at this problem.

SUMMARY OF THE INVENTION

A hand held syringe has a stationary handle and a moving handle to enable both stored and transported pharmaceuticals to be mixed and injecting the mixed pharmaceuticals under high pressure immediately after mixing through a long needle to a site interior of the body. The syringe is provided for squeeze grip at the stationary and moving handles between fingers and palm and includes a jell storage chamber side-by-side with a diluent storage chamber. First, the diluent is discharged to the jell mix chamber along a one way path. At the same time, a handle actuated piston loosely fitting to the side walls of the jell mix chamber moves through the jell and introduced diluent effecting mixing movement by allowing the jell and diluent to flow between the piston and jell chamber sidewalls. Flow occurs from the jell chamber by the piston to an expansible chamber delimited by a floating seal. This motion is repeated until thorough mixing occurs—a state which the operator can detect because of lowered viscosity and consequent easing of the effort required for the mixing motion. When injection is desired, the syringe is fully expanded against the spring bias. The perimeter of the piston is expanded against the gel storage chamber sidewalls. In the preferred embodiment, opposed flanges having a radially exposed V-shape, compress and dilate an O-ring on the piston radially outward. Such compression continues until an O-ring on the reciprocating piston is tightened to radially dilate the O-ring to effect sealed wiping of the jell chamber. When full dilation of the O-ring has occurred, the long needle replaces a sealing plug at the distal end of the jell chamber of the syringe and injection occurs under the full squeeze force developed by the digits against the human palm.

BRIEF DESCRIPTION OF THE DRAWINGS

FIG. 4 is an expanded section at the piston illustrating the preferred O-ring and seal.

DESCRIPTION OF THE PREFERRED EMBODIMENT

In the following description herein, an outline will be followed. The main elements of the embodiment will first be summarily identified. Thereafter, a detailed description of each of these elements will be made—with major reference to the exploded view provided herewith. Finally, operation will be set forth. This operation will be discussed first with respect to the loading for transport and storage of the syringes here shown and secondly with use of the syringe assembly for mixture and usual injection.

Figure 1:
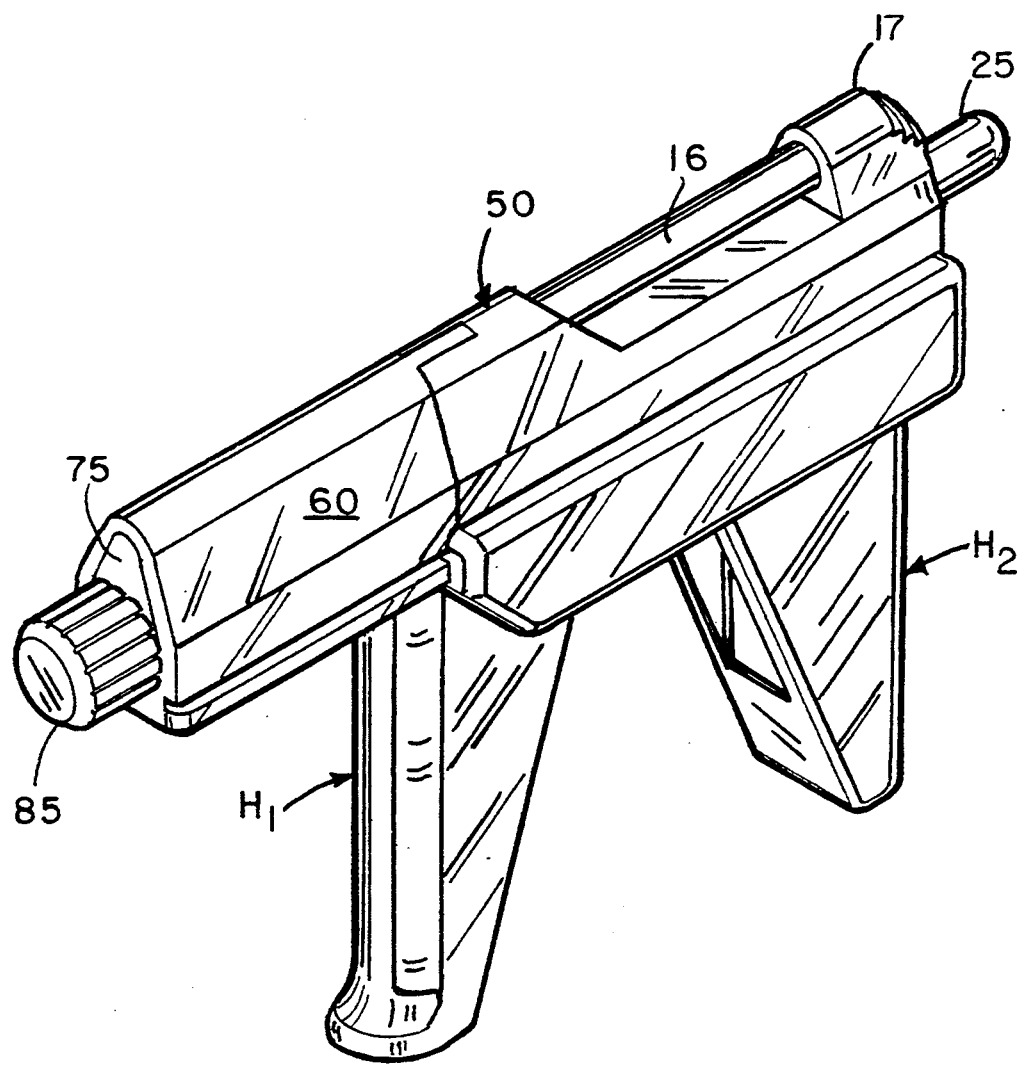
FIG. 1 is a perspective view of the hand held mixing syringe and high pressure injection discharge apparatus of this disclosure.
Figure 2:
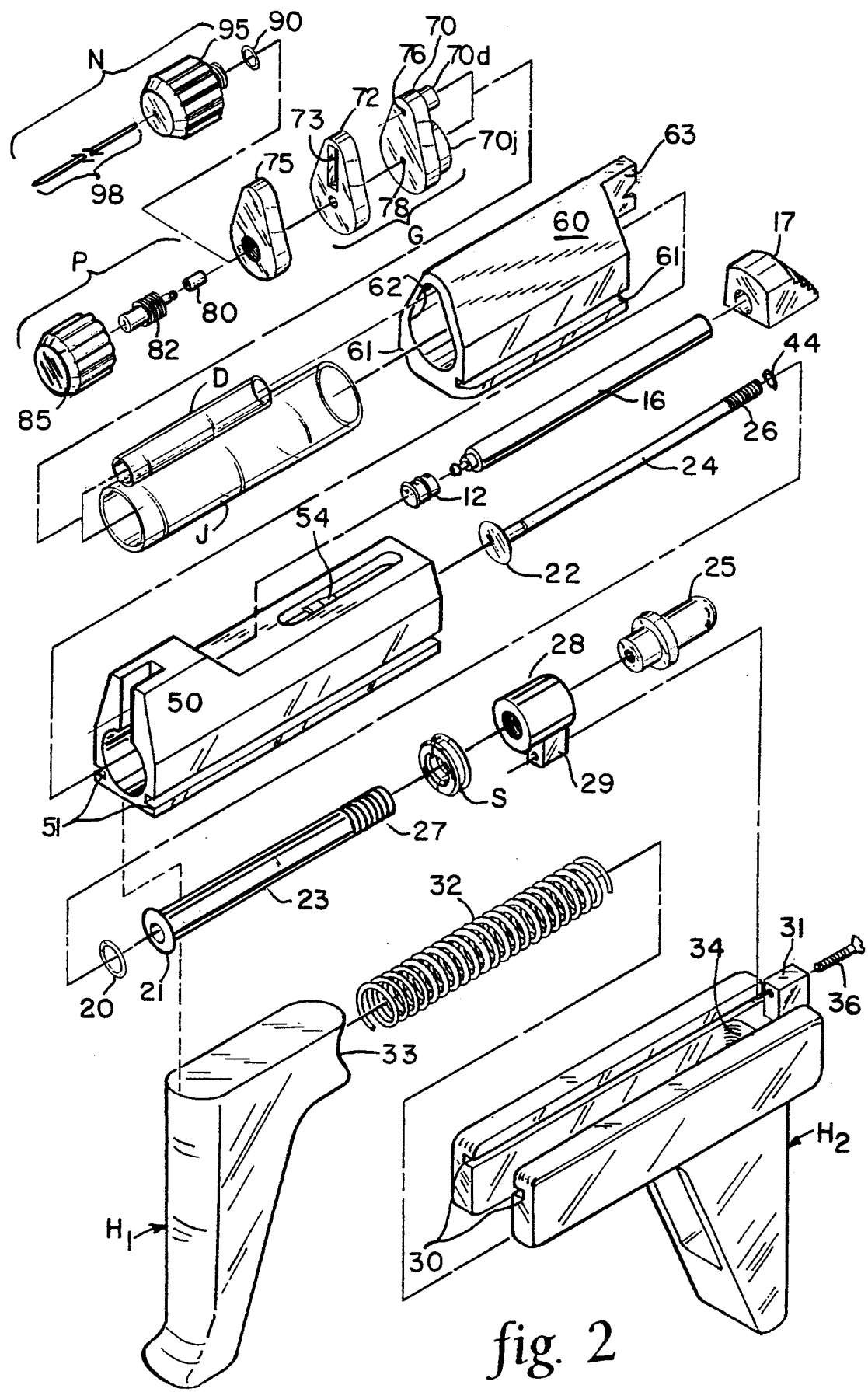
FIG. 2 is an exploded view illustrating the discrete parts of this invention in their respective exploded relation; and, FIG. 3 is a cross section of the hand held mixing syringe illustrating the respective portions of this invention.
Figure 3:
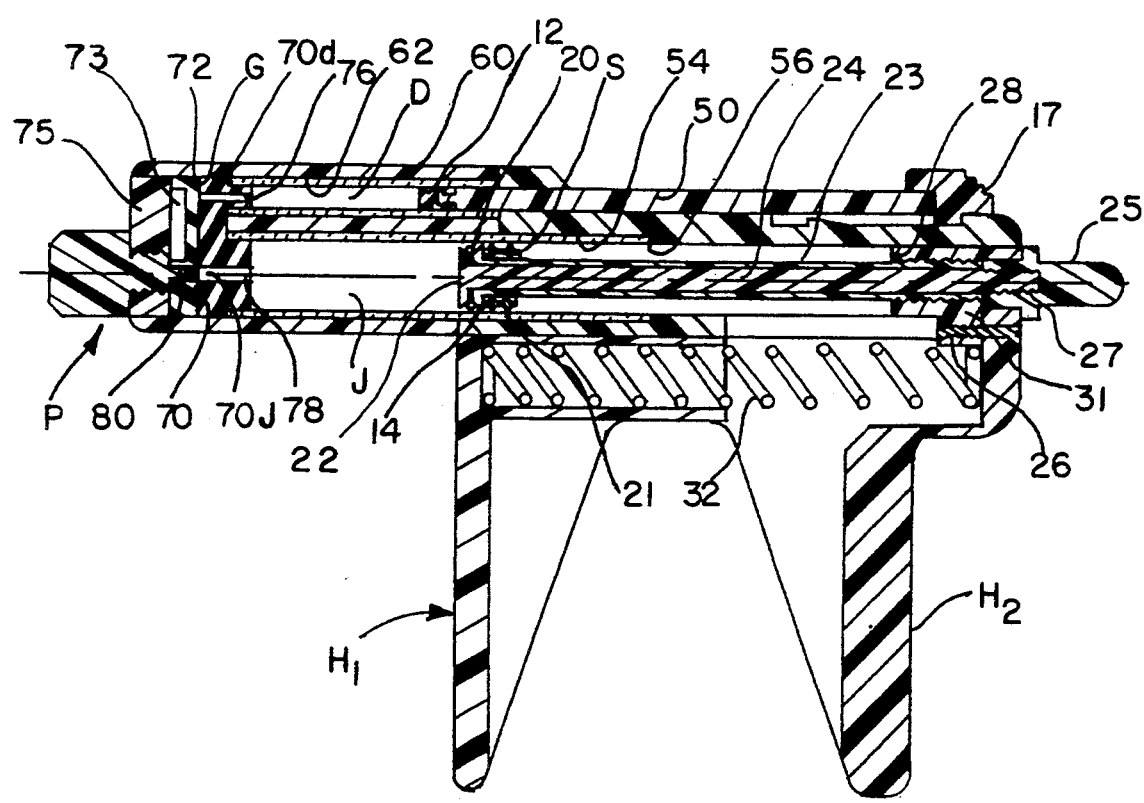
Figure 3A:
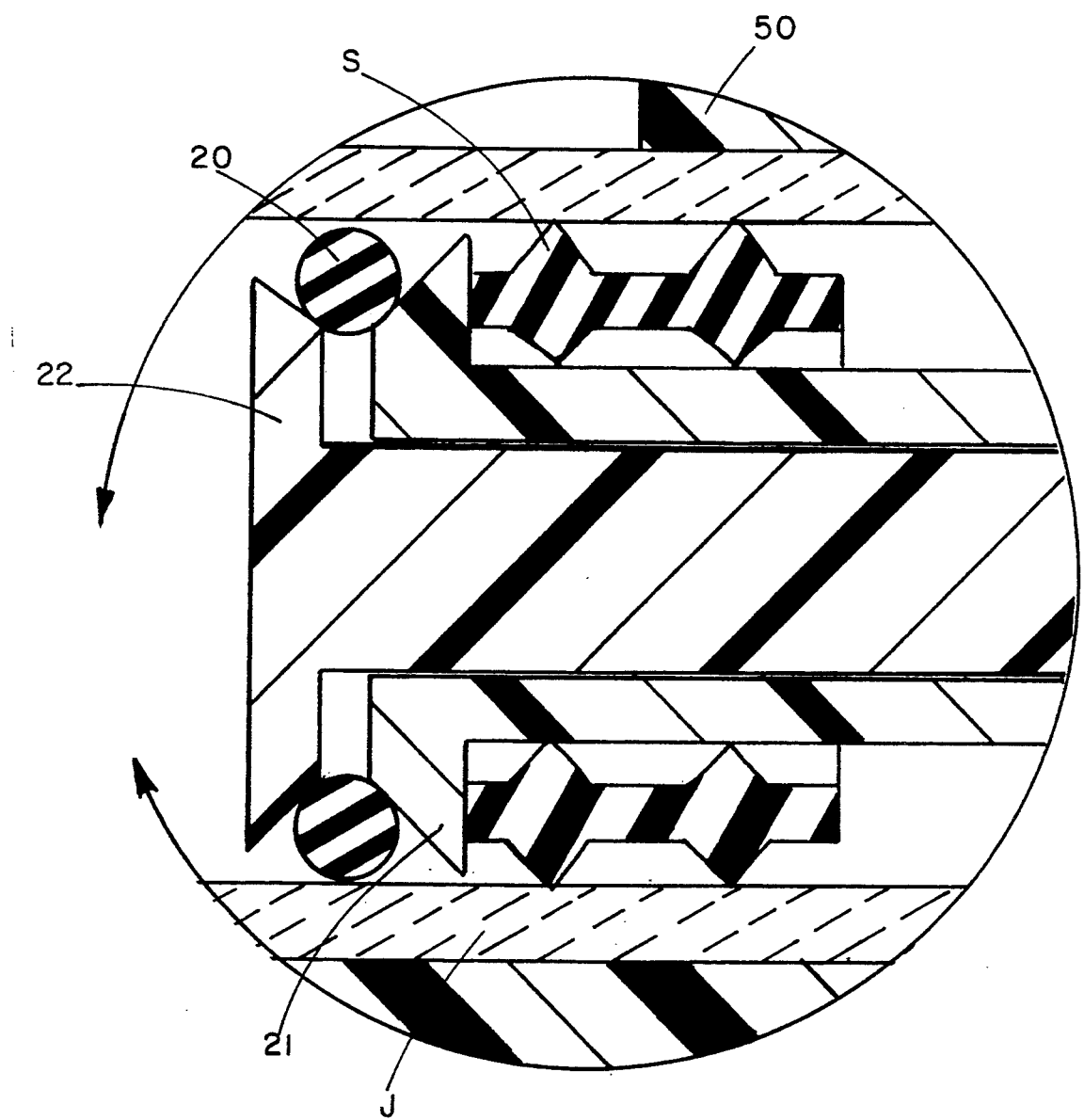

Referring to FIGS. 1–3, the primary operative portions of this invention can be understood. Handles $H_1$ for fitting to the palm of a human hand and handle $H_2$ for being grasped by the digits of the human hand are shown. It is to be understood that the syringe of this invention is held, mixed, and used for injection when firmly held by these handles.

The syringe includes a diluent storage chamber D and a jell storage chamber J. Diluent chamber D is discharged by a diluent piston 12. Jell storage chamber J is swept by a jell chamber piston 14. As will become more apparent hereafter, this piston can take on two configurations. In a first configuration, the piston moves within jell storage chamber J with clearance between the sidewalls of the chamber and piston 14. In this disposition, jell and diluent can be mixed. In a second configuration, the perimeter of piston 14 is dilated or expanded to sweep under a force fit the interior of the jell storage chamber 14. In this disposition, mixed jell and diluent can be expelled from the jell storage chamber under force exerted at the handles. Since the handles are typically grasped at the palm and digits, the force of expulsion can be sufficient to propel the mixture through an elongate needle having a range in the length of seven inches.

When diluent is first injected from diluent storage chamber D to jell storage chamber J, it is necessary to provide what is essentially a one way fluid path for the diluent. This is provided by confronted gasket members G. It will be understood that a mere check valve is not utilized for this function since it is required that until mixing is required, strict isolation be maintained between the diluent and jell.

It is required that before the handles are first brought together, that diluent displacing piston 12 be moved forwardly to effect discharge of diluent through one way gaskets G and into jell storage chamber J. This being the case, hammer 17 shoves diluent piston rod 16 forward which in turn causes piston 12 forward. Diluent discharge hammer 17 which fastens to handle section $H_2$ and when moved forward catches to cylinder aperture 54 to prevent reverse movement. It will be understood that this motion only occurs once—the piston 12 upon effecting discharge of the diluent does not repeat its single stroke.

The two functions of the moveable jell storage chamber piston can now be summarized. The main active member is O-ring 20. This O-ring is between two flanges—these respective flanges imparting a V-shaped profile radially of the O-ring 20. Cylinder flange 21 is attached to narrow cylinder 23. Rod flange 22 is attached to rod 24. By the expedient of turning a tightening nut 25 on threads 26, flange 22 is drawn on flange 21. Since O-ring 20 is therebetween, compression of the O-ring results. And since the respective flanges have a radially exposed V-shape, the O-ring is dilated outward. Such dilation takes the piston from a disposition where it passes the sides of jell storage chamber J with clearance to a disposition where it wipes the sides of jell storage chamber J. This wiping of the sides of jell storage chamber J can be made sufficiently snug to cause high pressure injection from the jell storage chamber.

When mixing movement of piston 14 in jell storage chamber J occurs, it is necessary to contain the fluid being mixed as it flows by piston 14. However, it will be noted that jell storage chamber J is occupied cylinder 23 and rod 24. Thus, on the proximal side of piston 14, provision has to be made for a variable length chamber. This is provided by floating seal S. Seal S wipes against jell storage chamber J on the outside and cylinder 23 on the inside. It prevents the communication of the jell and diluent being mixed exterior of the floating F and the syringe in general.

Once thorough mixing of the jell and diluent has occurred, it is necessary that provision be made for attachment of a needle for the high pressure injection which this invention allows. Accordingly, a dispensing passage plug P is provided. This dispensing passage plug P can be removed and needle assembly N fitted in its place. Once such fitting has occurred, injection may follow.

Having set forth the general construction of the syringe assembly of this invention, a detailed description of the component parts may now follow.

Handle $H_2$ forms the main support component of this syringe. It includes paired spaced apart female slides 30 for receiving male slides 51 on reciprocating body member 50. Reciprocating body member 50 fits to handle $H_1$.

Spring 32 is provided to bias handles $H_1$ and $H_2$ away, one from another. Spring 32 fits to depression 33 on handle $H_1$ and to depression 34 on handle $H_2$. It can be seen with the action of the spring 33 that the two handles move away one from another. Such motion assures that the palm and digits only need to move towards one another—movement away by the handles occurs under bias of the spring 33.

It is necessary that rod 23 be affixed relative to handle $H_2$. This occurs by cylinder threads 27 engaging cylinder holder 28. Cylinder holder 28 fastens at cylinder block 29 to mating cylinder block 31 on handle $H_2$ via screw 36. It is to be understood that floating seal S is captured on cylinder 23 and wipes the interior of jell storage chamber J during containing conforming movement as jell and diluent pass in mixing motion over cylinder 14.

Hammer 17, rod 16 and piston 12 are mounted on top of housing section 50. Before mixing movement occurs, hammer 17 is moved forward, moving rod 16 and piston 12 forward. Diluent is expelled from diluent storage chamber D.

A small rod O-ring 44 is provided. It is the function of this O-ring 44 to block any fluid flow path between rod 24 and cylinder 23. This flow path is open before compression of O-ring 20. Further, upon compression of O-ring 20, a flow path can remain, which flow path will again be blocked by O-ring 44.

Cylinder J fits interior of reciprocating body member 50 at cylinder aperture 54. The cylinder effects penetration of aperture 54 until contact with stop 56 is made.

A second reciprocating body member 60 fastens coaxially of reciprocating body member 50. This member includes male slide members 61 for fitting to female slide members 30. It further includes an elongated aperture 62. It is the function of elongated aperture 62 to hold diluent storage chamber D in overlying relation relative to jell storage chamber J.

Reciprocating body member 50 and second reciprocating body member 60 are keyed together. Specifically, a male key 63 on second reciprocating body member 60 fits in a female keyway on reciprocating body member 50.

When the respective diluent storage chamber D and jell storage chamber J are fitted one to another, they must be plugged. Such plugging occurs at double plug fitting 70 having diluent plug $70_D$ and jell plug $70_J$. These plugs each have centrally there of a diluent aperture 76 and a jell aperture 78.

It is required that a one way flow path from diluent aperture 76 through jell aperture 78 and into jell storage chamber be provided. This is necessary so that on first movement of the handles $H_1$ and $H_2$ towards each other that one way expulsion of the diluent occur. According, there is confronted to diluent aperture 76 and jell aperture 78 double plug gasket 72 having partial communication slot 73. This double plug gasket 72 and partial communication slot 73 serve two purposes.

First, and during transport and storage, it is required that an absolute seal be maintained between diluent and jell. This being the case, double plug fitting 70, double plug gasket 72, and end plug fitting 75 with plug P threaded into it maintain this seal.

Second, diluent must flow from diluent storage chamber D into jell storage chamber J. In this latter case, groove 73 provides only a partial, but not complete, passage between diluent aperture 76 and jell aperture 78. However, the thin strip of material between the end of groove 73 and jell aperture 78 deforms. And when this deformation occurs, the diluent of low viscosity readily enters jell aperture 78 and into gel storage chamber J.

Plug assembly P is relatively easy to understand. It includes stopper 80, threaded plug holder 82 and turning knob 85. Similarly, needle assembly N is easy to understand. It includes O-ring 90, knob 95 and needle 98.

Having set forth the exploded view, operation can now be explained. First loading of the syringe will be discussed. Thereafter, operation will be set forth.

Regarding the charging of the syringe with diluent and jell, the syringe is assembled save and except for double aperture plug 70, double plug gasket 72 and end plug fitting 75. In this state the correct amounts of diluent and Jell are metered into the respective jell storage chamber J and diluent storage chamber D. Thereafter, the double aperture plug 70, double plug gasket 72, end plug fitting 75 together with the assembled plug P are placed and sealed over the end of the syringe. It is in this disposition that transport and storage of the syringe occurs.

Just before injection—and when mixing is required—handles $H_1$ and $H_2$ are manipulated one towards another. Before the first stroke, diluent plunger 12 is shoved forward at hammer 17 through rod 16 to make its first and only stroke of diluent storage chamber D. Diluent passes out diluent aperture 76 in double plug fitting 70, along partial slot 73 in double plug gasket 72 and into jell storage chamber J through jell aperture 78. With the introduced diluent, enhancing mixture of the jell and diluent may occur.

Thereafter, handles $H_1$ and $H_2$ are moved towards each other to effect mixing by the user's grip being applied to the handles. When the user's grip is relaxed, spring 32 allows handles $H_1$ and $H_2$ to move away from one another under the expanding bias of the compressed spring 32.

It will be remembered that cylinder 14 at O-ring 20 has a normal diameter that clears the sides of jell storage chamber J. Accordingly, the jell and diluent will pass between the chamber sides and cylinder 14 periphery.

This passage is tight—and will require user effort on handles $H_1$ and $H_2$. However, as mixing occurs, this action will occur with less effort signaling that complete mixture is occurring.

It will be understood that the relative motion between the handles occurs with compression of spring 32. This being the case, release of the digits of the hand will allow handles $H_1$ and $H_2$ to move away one from another.

During this movement, sliding seal S will be active about the periphery of cylinder 24 and the interior of jell storage chamber J. It will confine the mixed jell and diluent and prevent general leakage from the syringe unit.

Finally, when sufficient mixture has occurred, handles $H_1$ and $H_2$ will be released. Spring 32 will expand the handles away from one another. Piston 14 will move distally of jell storage chamber J. At the same time, floating seal S will return to its normal juxtaposed position adjacent cylinder 14. Plug P will be removed; needle assembly N will be inserted to end plug member 75. All will be in readiness for injection.

In preparation for injection, nut 25 will be tightened on rod 24. Flange 22 will draw O-ring 20 onto flange 21. O-ring 20 will dilate radially outward. The syringe will be prepared for high pressure injection.

Thereafter, the syringe will be grasped at handles $H_1$ and $H_2$ and needle 98 inserted to the body site. The relatively wide spacing of handles $H_1$ and $H_2$ will assist this direction. When the end of the needle 98 is at the injection site, handles $H_1$ and $H_2$ will be moved towards one another. Injection will occur.

The reader will understand that this invention can admit of modification. In the present disclosure, mixing of diluent and jell has occurred without alternation between discrete syringe subassemblies. Instead, insertion of diluent has first occurred to the jell. Thereafter, by the expedient of using the expansible piston, mixing and injection can sequentially occur. Devices providing mixing and injection utilizing this combination are clearly intended to be within the scope of this disclosure.

We have also only shown one particular type of piston having an expansible perimeter. The particular device illustrated was an O-ring captured between flanges. The flanges have a V-shaped radial groove with the "V" exposed peripherally. Other types of pistons having expansible perimeters are contemplated by this disclosure. For example, V-belt shaped rubber rings could be used. Further, virtually any type of member which can radially dilate will suffice.

Further, and regarding the method of dilation, any strategy will suffice. We have illustrated mechanical compression. The reader should realize that inflation or expansion of a bladder type member would work as well. Virtually any expedient for causing the piston to move in peripheral diameter from a mixing diameter to a wiping diameter for the injection disclosed herein will suffice.

In the preferred embodiment, we illustrate high pressure injection. Low pressure injection is included. Further, we illustrate handles for occupying the palm and combined digits. It will be apparent that this invention could as well be utilized with digit depressed flanges—and are commonly found in conventional syringes.

What is claimed is:

1. A hand held pharmaceutical storage and mixing syringe having high pressure assisted discharge comprising:

first and second relatively moveable handles constructed for movement relative to one another;

a jell storage chamber having a dispensing opening and parallel sidewalls affixed to said first handle for coaction with a moving jell storage chamber piston;

a diluent storage chamber having an outlet at one end with parallel sidewalls and a diluent displacing piston;

means for defining a one way fluid flow path from said diluent storage chamber outlet to said jell storage chamber;

means for moving said diluent displacing piston toward said diluent outlet connected for actuation by relative movement between said handles to expel diluent from said diluent storage chamber to said jell storage chamber;

a moveable jell storage chamber piston affixed to said second handle having a perimeter for movement along the walls of said jell storage chamber responsive to movement between said handles, means for providing said jell storage chamber piston with an expansible perimeter, said means providing to said piston a first normally contracted perimeter for causing fluid within said jell storage chamber to flow between the sides of said jell storage chamber and said piston to effect mixing of the contents within said jell storage chamber and a second expanded disposition for expelling the contents of said jell storage chamber under pressure;

means for containing mixed diluent and jell flowing by said piston during mixing movement of said piston in said jell storage chamber;

a dispensing passageway from said jell chamber, said dispensing passageway having a removable seal for permitting dispensing of the contents of said jell storage chamber upon seal removal; and, means for expanding the perimeter of said piston whereby when said handles are moved relative to one another expulsion of the contents of said jell chamber occurs.

2. A hand held pharmaceutical storage and mixing syringe according to claim 1 and wherein:

one of said relatively moving handles is configured for placement against the palm of a human hand and the other of said relatively moving handles is configured for placement against the combined digits of a human hand.

3. A hand held pharmaceutical storage and mixing syringe according to claim 1 and wherein:

said means for defining said one way fluid flow path includes first and second rubber members confronted one to another, said members as confronted defining a path from said diluent storage chamber to said jell storage chamber.

4. A hand held pharmaceutical storage and mixing syringe according to claim 1 and wherein said means for providing said jell storage chamber piston with an expansible perimeter includes:

an expansible O-ring having a normal diameter corresponding to said first normally contracted perimeter;

means for dilating said jell storage chamber O-ring connected to said piston, said means for dilating said O-ring between said first normally contracted perimeter to said second and expanded disposition for expelling said contents of said jell storage chamber.

5. A hand held pharmaceutical storage and mixing syringe according to claim 4 and wherein:

said means for dilating said O-ring includes paired flanges with said O-ring therebetween, said flanges having a V-shaped section for receiving said O-ring therebetween; and, means for urging said flanges towards one another whereby said flanges when urged together expand said O-ring by dilating said O-ring into contact with the walls of said jell storage chamber.

6. A hand held pharmaceutical storage and mixing syringe according to claim 1 and wherein:

said means for containing mixed diluent and jell includes a floating seal in said jell storage chamber, said floating seal enabling movement of said jell storage chamber piston along said jell storage chamber between an end of said jell storage chamber and said floating seal.

7. A hand held pharmaceutical storage and mixing syringe according to claim 6 and further including:

a rod communicated to said second handle and extending into said jell storage chamber; and, said floating seal moves along said rod at an inner perimeter of said seal and along the sidewalls of said chamber at an outer perimeter of said seal.

8. A hand held pharmaceutical storage and mixing syringe according to claim 1 and wherein:

said removable seal on said dispensing passageway defines an aperture for mounting a needle when said seal is removed.

9. A hand held pharmaceutical storage and mixing syringe according to claim 1 and further including a rod;

said moveable jell storage chamber piston connected to said handle by said rod, said rod extending into said jell storage chamber;

said rod including a first relatively moveable portion and a second relatively moveable portion;

a first flange attached to one of said relatively moveable portions;

a second flange attached to said other relative moveable portion; and, said means for providing said jell storage chamber with an expansible perimeter affixed between said flanges, said means for providing said cylinder with an expansible perimeter responsive to movement of said flanges toward one another under force.

10. A hand held pharmaceutical storage and mixing syringe according to claim 9 and wherein:

said means for moving said relatively moveable members of said piston rod together includes a threaded member threaded to one of said piston rod portions and bearing on the other of said piston rod portions.

11. A method for hand held pharmaceutical storage, mixing and syringe injection with high pressure assisted discharge comprising:

providing first and second relatively moving actuators for relative movement to one another;

providing a jell storage chamber having a dispensing opening and parallel sidewalls affixed to said first actuator for coaction with a moving jell storage chamber piston;

providing a diluent storage chamber having an outlet at one end with parallel sidewalls for coaction with a diluent displacing piston;

defining a one way fluid flow path from said diluent storage chamber outlet to said jell storage chamber;

displacing said diluent displacing piston toward said diluent outlet to expel diluent from said diluent storage chamber to said jell storage chamber;

providing a moveable jell storage chamber piston affixed to said second actuator having a perimeter for movement along the walls of said jell storage chamber responsive to movement between said actuators;

providing said jell storage chamber piston with an expansible perimeter, including a first normally contracted perimeter for causing fluid within said chamber to flow between the sides of said jell storage chamber and said piston to effect mixing of the contents within said jell storage chamber and a second expanded disposition for expelling the contents of said jell storage chamber under pressure;

containing mixed diluent and jell flowing by said piston during mixing movement of said piston in said jell storage chamber;

providing a dispensing passageway from said jell chamber including, said dispensing passageway having a removable seal for permitting dispensing of the contents of said jell storage chamber upon seal removal;

moving said actuators towards and away from one another with said piston having said perimeter in said normal contracted state to mix said diluent and jell;

expanding the perimeter of said piston;

removing said seal from said dispensing passageway; and, moving said actuators relative to one another until expulsion of the contents of said jell chamber occurs.

12. A method for hand held pharmaceutical storage, mixing and syringe injection with high pressure assisted discharge according to claim 11 and including the steps of:

placing one of said relatively moving actuators against the palm of a human hand and placing the other of said relatively moving actuators against the combined digits of a human hand.

13. A method for hand held pharmaceutical storage, mixing and syringe injection with high pressure assisted discharge according to claim 11 and including the steps of:

placing a needle to said seal of said dispensing passageway after said moving said actuators step.

14. A hand held pharmaceutical storage and mixing syringe having high pressure assisted discharge comprising:

first and second relatively moving actuators for relative movement to one another;

a first pharmaceutical storage chamber having a dispensing opening and parallel sidewalls affixed to said first actuator for coaction with a first pharmaceutical storage chamber piston;

a second pharmaceutical displacing piston;

a second pharmaceutical storage chamber having an outlet at one end with parallel sidewalls for coaction with said second pharmaceutical displacing piston;

means for defining a one way fluid flow path from said second pharmaceutical storage chamber outlet to said first pharmaceutical storage chamber;

means for moving said second pharmaceutical displacing piston toward said second pharmaceutical outlet connected for actuation by relative movement between said actuators to expel second pharmaceutical from said second pharmaceutical storage chamber to said first pharmaceutical storage chamber;

a moveable first pharmaceutical storage chamber piston affixed to said second actuator having an perimeter for movement along the walls of said first pharmaceutical storage chamber responsive to movement between said actuators;

means for providing said first pharmaceutical storage chamber piston with an expansible perimeter, said means providing to said piston a first normally contracted perimeter for causing fluid within said chamber to flow between the sides of said first pharmaceutical storage chamber and said piston to effect mixing of the contents within said first pharmaceutical storage chamber and a second expanded disposition for expelling the contents of said first pharmaceutical storage chamber under pressure;

means for containing mixed second pharmaceutical and first pharmaceutical flowing by said piston during mixing movement of said piston in said first pharmaceutical storage chamber;

a dispensing passageway from said first pharmaceutical chamber, said dispensing passageway having a removable seal for permitting dispensing of the contents of said first pharmaceutical storage chamber upon seal removal; and, means for expanding the perimeter of said piston whereby when said actuators are moved relative to one another expulsion of the contents of said chamber occurs.

15. A hand held pharmaceutical storage and mixing syringe having high pressure assisted discharge comprising:

first and second relatively moving actuators for relative movement to one another;

a first pharmaceutical storage chamber having a dispensing opening and parallel sidewalls affixed to said first actuator for coaction with a moveable first pharmaceutical storage chamber piston;

a first pharmaceutical in said first pharmaceutical storage chamber;

a second pharmaceutical storage chamber having an outlet at one end with parallel sidewalls and a second pharmaceutical displacing piston;

a second pharmaceutical in said second pharmaceutical storage chamber;

means for defining a one way fluid flow path from said second pharmaceutical storage chamber outlet to said first pharmaceutical storage chamber;

means for moving said second pharmaceutical displacing piston toward said second pharmaceutical outlet connected for actuation by relative movement between said actuators to expel second pharmaceutical from said second pharmaceutical storage chamber to said first pharmaceutical storage chamber;

a moveable first pharmaceutical storage chamber piston affixed to said second actuator having an perimeter for movement along the walls of said first pharmaceutical storage chamber responsive to movement between said actuators;

means for providing said first pharmaceutical storage chamber piston with an expansible perimeter, said means providing to said first piston a first normally contracted perimeter for causing fluid within said chamber to flow between the sides of said first pharmaceutical storage chamber and said piston to effect mixing of the contents within said first pharmaceutical storage chamber and a second expanded disposition for expelling the contents of said first pharmaceutical storage chamber under pressure;

means for containing mixed second pharmaceutical and first pharmaceutical flowing by said piston during mixing movement of said piston in said first pharmaceutical storage chamber;

a dispensing passageway from said first pharmaceutical chamber, said dispensing passageway having a removable seal for permitting dispensing of the contents of said first pharmaceutical storage chamber upon seal removal; and, means for expanding the perimeter of said piston whereby when said actuators are moved relative to one another expulsion of the contents of said first pharmaceutical chamber occurs.

16. A method for hand held pharmaceutical storage, mixing and syringe injection with high pressure assisted discharge where the syringe includes:

first and second relatively moving actuators for relative movement to one another;

a first pharmaceutical storage chamber having a dispensing opening and parallel sidewalls affixed to said first actuator for coaction with a moveable first pharmaceutical storage chamber piston;

a second pharmaceutical storage chamber having an outlet at one end with parallel sidewalls and a second pharmaceutical displacing piston;

a one way fluid flow path from said second pharmaceutical storage chamber outlet to said first pharmaceutical storage chamber;

a first pharmaceutical in said first pharmaceutical storage chamber;

a second pharmaceutical in said second pharmaceutical storage chamber;

said method comprising the steps of:

displacing said second pharmaceutical displacing piston toward said second pharmaceutical outlet to expel second pharmaceutical from said second pharmaceutical storage chamber to said first pharmaceutical storage chamber;

providing a moveable first pharmaceutical storage chamber piston affixed to said second actuator having an perimeter for movement along the walls of said first pharmaceutical storage chamber responsive to movement between said actuators;

providing said first pharmaceutical storage chamber piston with an expansible perimeter, said means providing to said piston a first normally contracted perimeter for causing fluid within said chamber to flow between the sides of said first pharmaceutical storage chamber and said piston to effect mixing of the contents within said first pharmaceutical storage chamber and a second expanded disposition for expelling the contents of said first pharmaceutical storage chamber under pressure;

containing mixed second pharmaceutical and first pharmaceutical flowing by said piston during mixing movement of said piston in said first pharmaceutical storage chamber;

providing a dispensing passageway from said first pharmaceutical chamber, said dispensing passageway having a removable seal for permitting dispensing of the contents of said first pharmaceutical storage chamber upon seal removal;

moving said actuators towards and away from one another with said piston having said perimeter in said normal contracted state to mix said second pharmaceutical and first pharmaceutical;

expanding the perimeter of said piston;

removing said seal from said dispensing passageway; and, moving said actuators relative to one another until expulsion of the contents of said first pharmaceutical chamber occurs.

17. A hand held pharmaceutical storage and mixing syringe according to claim 14 further comprising said first and second pharmaceuticals and wherein said first pharmaceutical comprises a jell and said second pharmaceutical comprises a diluent.

18. A hand held pharmaceutical storage and mixing syringe according to claim 14 and wherein said first and second relatively moving actuators include a first actuator for fitting to the human palm and a second actuator for grasp by the human digits.

19. A hand held pharmaceutical storage and mixing syringe according to claim 17 and wherein said means for moving said diluent displacing piston includes a sliding member moveable into said piston.

20. A hand held pharmaceutical storage and mixing syringe according to claim 17 and wherein said means for providing said jell storage chamber with an expansible perimeter includes first and second flanges with an O-ring disposed therebetween, a rod;

a cylinder bed rod;

said first flange connected to said rod;

said second flange connected to said cylinder bed rod, and further including a third member having a thread connection to said rod, bearing on said cylinder bed rod, and biasing said cylinder bed rod toward said first flange.

21. A hand held pharmaceutical storage and mixing syringe according to claim 17 and wherein said means for containing mixed diluent and jell includes a floating member in said first pharmaceutical storage chamber.

22. A hand held pharmaceutical storage and mixing syringe according to claim 17 and wherein said means for providing said storage chamber piston with an expansible perimeter includes a rod including and extending to a first flange, a cylinder including and extending to a second flange, and means for compressing said rod to said cylinder and said means for containing mixed diluent includes a seal, said seal bearing on said cylinder on the inside and on said jell storage chamber on the outside.

23. A hand held pharmaceutical storage and mixing syringe according to claim 14 and wherein said dispensing passageway includes an attachment point for a needle.

24. A hand held pharmaceutical storage and mixing syringe according to claim 15 and wherein said first pharmaceutical comprises a jell and said second pharmaceutical comprises a diluent.

25. A hand held pharmaceutical storage and mixing syringe according to claim 24 and wherein said jell includes a cytotoxin and bulking agent and said diluent includes a vasoconstricting agent.

26. A hand held pharmaceutical storage and mixing syringe according to claim 24 and wherein said means for defining a one-way fluid flow path from said diluent storage chamber outlet to said jell storage chamber includes an elastic member defining a channel, said channel beginning at said diluent storage chamber outlet and extending to said jell storage chamber dispensing opening, said member stopping short of said jell storage chamber dispensing opening and being deformable responsive to pressure exerted on said diluent.

27. A method for hand held pharmaceutical storage, mixing and syringe injection according to claim 16 and wherein said first pharmaceutical comprises a jell and said second pharmaceutical comprises a diluent.

28. A method for hand held pharmaceutical storage, mixing and syringe injection according to claim 16 including the steps of:

moving said actuators towards and away from another to tactilely detect decreased resistance of said movement indicating complete mixing.

29. A method for hand held pharmaceutical storage, mixing and syringe injection according to claim 27 and including the step of:

providing a needle, and attaching said needle to said dispensing passageway for injection of said mixed diluent and jell.

* * * * *